Figure 1:
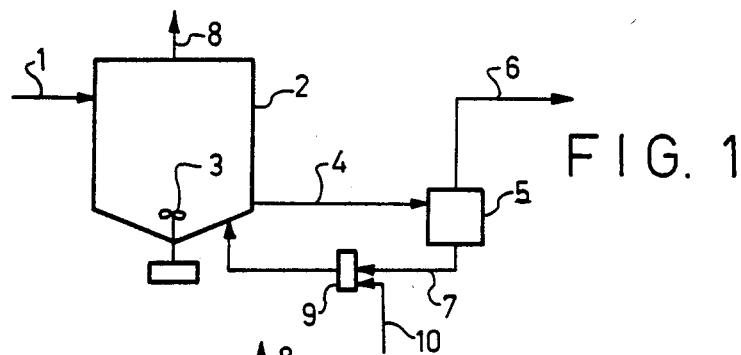

United States Patent [19]

Da Silva Telles et al.

[11] Patent Number: 4,889,805
[45] Date of Patent: Dec. 26, 1989

[54] CONTINUOUS PROCESS OF OPTIMIZED FERMENTATION FOR THE PRODUCTION OF ALCOHOL

[76] Inventors: Affonso C. S. Da Silva Telles, R. Prof. Sabóia Ribeiro No 83/404, Leblon, Rio de Janeiro; Claudio M. Váz, R. Humaitá No 406/1.002, Botafogo, Rio de Janeiro, both of Brazil

[21] Appl. No.: 189,750

[22] Filed: May 3, 1988

[30] Foreign Application Priority Data

May 20, 1987 [BR] Brazil ..................... 8702590

[51] Int. Cl.$^4$ .......................... C12P 7/06; C12R 1/865
[52] U.S. Cl. ..................... 435/161; 435/813; 435/942
[58] Field of Search ................ 435/161, 942, 813

[56] References Cited

U.S. PATENT DOCUMENTS

| | | | |
|---|---|---|---|
| 4,358,536 | 11/1982 | Thorsson et al. | 435/161 |
| 4,460,687 | 7/1984 | Ehnstrom | 435/161 |

FOREIGN PATENT DOCUMENTS

| | | | |
|---|---|---|---|
| 3542246 | 6/1987 | Fed. Rep. of Germany | 435/161 |
| 0015691 | 2/1981 | Japan | 435/161 |
| 0085294 | 5/1984 | Japan | 435/161 |
| 294133 | 1/1927 | United Kingdom | 435/161 |
| 2059988 | 4/1981 | United Kingdom | 435/161 |
| 2065699 | 7/1981 | United Kingdom | 435/161 |

OTHER PUBLICATIONS

Ramirez, A. et al., "Continuous Production of Ethanol on Beet Juice by a Flocculant Strain of Saccharomyces Cerevisiae", Biotech Lett 5 (10), pp. 659–665 (1983).

Biotech Abstract 83-10529, Ramirez et al., Biotech Lett. (1983) 5, 10, 659–664.

*Primary Examiner*—Herbert J. Lilling
*Attorney, Agent, or Firm*—Beveridge, DeGrandi & Weilacher

[57] ABSTRACT

A continuous process of optimized fermentation of sugars for the production of alcohol is disclosed, which comprises the following process steps and operational conditions:

(a) continuously feeding a wort with a controlled concentration of sugars in the range of 100 to 160 g/l into one or more fermentation vessels arranged in parallel and containing a culture with a concentration of yeast cells in the range of $10^{11}$ to $10^{12}$ cells per liter, and completely stirring the fermentation medium;

(b) controlling the conditions of the fermentation medium by fixing the temperature in the range of 30° to 39° C. and the pH in the range of 3.2 to 4.5;

(c) continuously removing from the fermenter a stream of wine obtained from the wort fermentation so as to keep the retention time in the fermenter fixed in the range of 4 to 9 hours; and (d) separating the stream of wine leaving the fermenter into a substantially yeast-free stream and a yeast-concentrated stream, said yeast-containing stream being recirculated into the fermenter and said substantially yeast-free stream being sent to subsequent processing for the recovery of the alcohol. Before being recirculated into the fermenter, the yeast-concentrated stream can be subjected to an optional treatment with an acid during a short period of time.

7 Claims, 1 Drawing Sheet

CONTINUOUS PROCESS OF OPTIMIZED FERMENTATION FOR THE PRODUCTION OF ALCOHOL

The present invention refers to a continuous and homogeneous fermentation process in optimized conditions for the production of alcohol, which has a high fermentation yield and consequently a high efficiency in the production of alcohol.

With the increase in the demand for alcohol, particularly due to increased utilization thereof as a fuel, various processes have been developed with a view efficiently to supply this increase in the demand. Among the alternatives proposed in the art, a special approach has been made to continuous alcohol-fermentation processes, owing to the advantages which they can provide with respect to conventional batch processes.

Thus, in the Brazilian Pat. No. PI 7901546, a continuous alcohol-fermentation process is presented which utilizes selected microorganisms (yeasts) having a high reproduction capacity and a high resistance to the ethanol produced during the fermentation. The process described therein can be carried out in a single fermentation vessel or also in a set of fermentation vessels arranged in series. An intitial step of such a process consists of the adaptation of the yeast (during 3 to 6 days) to the fermentation medium through special conditions and, after such a step, in permanent regime, air is blown into the fermenting medium and the initial concentration of sugars in the wort of the adaptation phase is increased to 300 g/l.

The fermented wine is then discharged and separated into a stream containing used microorganisms, which is recirculated into the fermenter, and a stream containing alcohol, which does on to distillation. The combination of the above-mentioned conditions in the process disclosed in Patent PI 7901546 aims, on the one hand, at the obtention of a stillage with a high concentration (that is, reduction of the volume of stillage produced) and, on the other hand, a higher productivity of the installation (that is, reduction of the volume of the fermentation vessel).

Thus, among other things, with a view to the reduction of the stillage produced, the process disclosed in Patent PI 7901546 uses a high sugar content wort—300 g/l—which leads to a high alcohol concentration in the fermentation medium. Usually this is extremely detrimental to the fermentation microorganism. It is believed that this is the reason why the patent mentions that "selected microorganisms with a high reproduction rate and a high resistance to ethanol" are used, although they are not specifically defined. More specifically, specially selected microorganisms should be used in order to support the high alcohol concentration generated in the fermentation.

On the other hand, blowing air into the fermenting medium, as described in Patent PI 7901546, will cooperate with the increase in the reproductivity of the microorganisms (aerobic growth phase), which will therefore result in a greater sugar consumption in the wort for the formation of new cells and the consequent reduction of the sugar available for the formation of alcohol, thus causing a reduction of the yield of the process.

As described in Patent PI 7901546, vats or fermentation vessels arranged in series can be used too. However, this is not adequate for the fermenting microorganisms since, in this arrangement, they are often subjected to constant variations in their fermentation environment conditions.

Due to these disadvantages a satisfactory fermentation yield in the process of Patent PI 7901546 cannot be obtained.

Another continuous alcohol fermentation process is described in the Brazilian patent application PI 7900321, which consists in fermenting the wort in one or more than one fermentation vats or vessels arranged in series, separating the fermented stream into a yeast-free stream, and recirculating the yeast-concentrated stream into the fermentation vessel; the yeast-free stream is separated into a volatile organic component-rich stream and a residual stream, at least a portion of the latter being recirculated to the fermenter.

The process of Patent PI 7900321 essentially aims, among other things, at reducing the volume of the stillage produced, and for this purpose a portion of said residual stream is recirculated into the fermenter. However, this recirculation provides an increase in the concentration of salts in the fermentation medium, thereby negatively affecting the fermentation yield.

Therefore, considering on the other hand that the overall yield in the alcohol producing process constitutes a factor that determines the economy of the process, it becomes imperative to provide a continuous fermentation process that aims at the optimization of the fermentation yield, that is, a better yield in the production of alcohol.

Thus, an object of the present invention is to provide a continuous alcohol fermentation process which is simple and provides a high fermentation yield, without, however, showing the disadvantages mentioned above which occur in the processes known to the prior art.

Therefore, as a result of intense research and experiments, a new continuous alcohol fermentation process has now been developed which, unlike most other existing processes, is essentially directed to the optimization of the fermentation yield (alcohol mass produced/sugar mass consumed)—consequently a greater yield in the production of alcohol—using two basic principles, namely:

(1) keeping the fermentation conditions as appropriate as possible for the production of alcohol; and
(2) keeping a fermentation medium as homogeneous and constant as possible around the fermenting microorganism.

This is achieved in an effective and efficient manner with the process of the present invention by combining certain fermentation conditions with the utilization of simple processing steps and equipment, as described below.

The continuous optimized sugar-fermentation process for the production of alcohol according to the present invention is characterized in that it comprises the following process steps and operating conditions:

(a) continuously feeding a wort with a controlled concentration of sugars in the range of 100 to 160 g/l into one or more fermentation vessels arranged in parallel and containing a culture with a concentration of yeasts in the range of $10^{11}$ to $10^{12}$ cells per liter, and completely stirring the fermentation medium;

(b) controlling the conditions of the fermentation medium by fixing the temperature in the range of 30° to 39° C. and the pH in the range of 3.2 to 4.5;

(c) continuously removing from the fermenter a stream of wine obtained from the wort fermentation so as to keep the residence time in the fermenter fixed in the range of 4 to 9 hours; and (d) separating the stream of wine leaving the fermenter into a substantially yeast-free stream and a yeast-concentrated stream, said yeast-containing stream being recirculated to the fermenter and said substantially yeat-free stream being led to subsequent processing for recovery of the alcohol.

The term "completely stirring" as used here means a stirring necessary for maintaining homogeneous fermentation conditions in the medium.

According to the process of the present invention, the fermentation is carried out either in one fermentation vessel or in more than one fermentation vessels arranged in parallel—only one vessel being preferable—and, in the wine separation step there can be used any separating device which provides an adequate separation of the wine into a substantially yeast-free stream and a yeast-concentrated stream to be recirculated. For the separation step, for example, centrifugation separating devices may be used.

According to one embodiment of the invention, the yeast-concentrated stream separated in step (d) defined above can be optionally subjected to a treatment with an acid, before it is recirculated to the fermenter. This treatment is appropriate in the case that there is the possibility of flocculation of the yeast cells, but it is carried out, according to the invention, in a quite short period of time, and in a continuous manner. Thus, such an optional treatment does not have the disadvantages shown by the conventional processes.

The simplicity of the above-mentioned equipment and operations, in association with the combination of specific conditions used in the fermentation step in itself, provides the obtention of a uniform and constant environment that is highly favourable for the production of alcohol by the yeasts, besides providing easiness in controlling such conditions, whereby a significant improvement in the fermentation yield—alcohol mass produced/sugar mass consumed—is achieved. According to the present invention, an increase in fermentation yield higher than 5 percentage points with respect to the existing processes is obtained.

The process of the present invention is particularly appropriate for the production of ethanol.

At present, there are several microorganisms that can be used in fermentation for the production of alcohol; however, according to the process of the present invention, yeast of the genus SACCHAROMYCES is used, without, however, the obligatoriness of using special selected yeats, as is the case in some processes of the prior art. A particularly appropriate yeast is that of the genus SACCHAROMYCES, species CEREVISIAE.

The preferred fermentation conditions for carrying out the process of the present invention comprise a sugar content in the wort of about 130 g/l, a retention time of about 6 hours, a temperature of about 32° C., a pH of 4.0 and a concentration of yeast cells of $1.20 \times 10^{12}$ viable cells per liter.

The introduction of the wort in the fermentation vessel and the withdrawal of the fermented wine therefrom are carried out preferable through the top and the bottom, respectively.

After the separation step, the substantially yeast-free stream is led to subsequent recovery of the alcohol, through the usual mechanisms such as, for instance, distillation.

Figure 2:
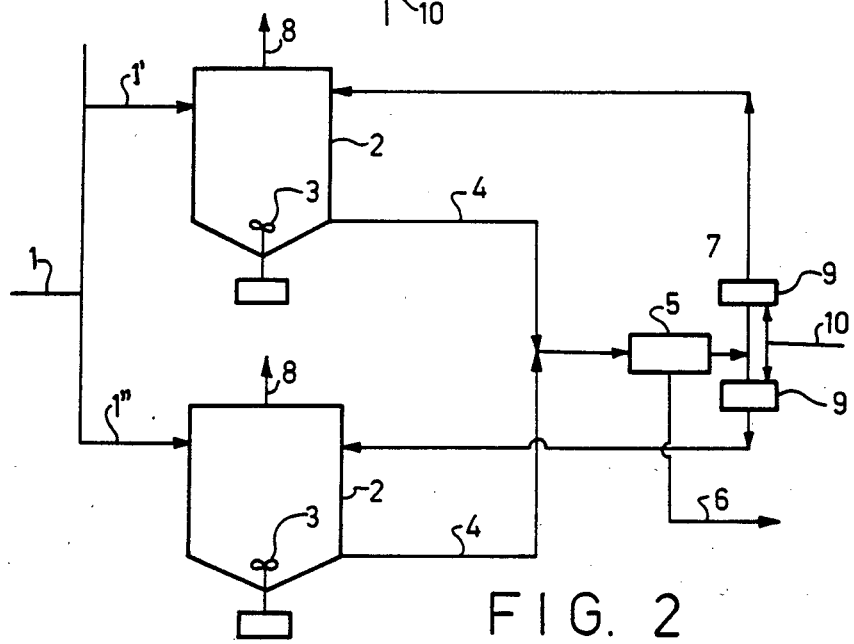

The process of the present invention is illustrated below through the process disgrams shown in the drawings, in which:

FIG. 1 illustrates how the process can be carried out in only one fermentation vessel; and FIG. 2 illustrates how the process can be carried out in fermentation vessels arranged in parallel.

As shown in FIG. 1, the wort is introduced, via line 1, into a fermentation vessel 2 provided with a stirring device 3. After the fermentation period, the wine is then taken out via line 4 and led to a separating device 5, where the wine is separated into a yeast-free stream 6 and a yeast-concentrated stream 7, which can be fed to an optional acid-addition device 9, and then is recirculated into the fermentation vessel 2. The acid solution for the optional treatment in the device 9 is made through the stream 10. The yeast-free stream 6 is then led to additional processing for removal of the alcohol contained therein. The $CO_2$ produced in the fermentation vessel 2 is discharged via line 8 or, if desired, is reutilized by usual methods.

FIG. 2 shows a process scheme in which two fermentation vessels arranged in parallel are used, the reference numerals having the same meaning as in FIG. 1, except the reference numerals 1' and 1", 7' and 7", which correspond to the division of the cited streams 1 and 7, respectively.

The continuous process of the present invention is further illustrated in the following example, which serves only to show the functioning of the present invention, without, however, being a limitative aspect of same.

EXAMPLE

A fermentation vat has been adapted for operation with the continuous fermentation process according to the present invention.

Initially a usual fermentation feedstock (yeasts of the type Saccharomyces) was put into the vat, and a total fermentation volume (35 m$^3$) was slowly completed with sugar-cane-juice wort, maintaining the fermentation BRIX below 4.0. After such a volume was attained, it was waited for the BRIX to fall to zero, and then the operation of removal and centrifugation of the fermented wine was started for the obtention of a substantially yeast-free stream and a yeast-concentrated stream, while, at the same time, the vat was fed with sugar-cane juice with controlled BRIX and kept at a constant level. The yeast-concentrated stream was recirculated to the vat while the yeast-free stream was led to the movable vat. The system operated for 9 days with approximately stabilized conditions, the average values of which are shown in Table I. During this period, a total amount of 71,523 kg ethanol was produced, and a total amount of 148,742 kg of total reducing sugars was consumed, thereby producing a fermentation yield of 94%.

In this same period, other vats were operated according to the conventional batch fermentation process, by using the same raw material that was used in the above example. An average fermentation yield of only 87% was attained. It should be pointed out that the existing continuous fermentation processes, when compared with the conventional batch fermentation process, have shown very close fermentation yields, and have even caused the false conclusion, which is so common in the alcohol production area, that there is no difference between the fermentation yields of the batch process and the continuous process, when, in reality, in a continuous and homogeneous process with optimized conditions, the yield can be significantly higher, as shown above.

TABLE I

Juice feeding rate - 5,6 m³/h
total reducing sugars in the juice - 12,6 g/100 g
fermentation temperature - 32-35° C.
fermentation pH - 4,0-4,5

We claim:

1. A continuous and homogeneous process of optimized fermentation of sugars for the production of alcohol, which comprises the following process steps and operational conditions:

(a) continuously feeding a wort with a controlled concentration of sugars in the range of 100 to 160 g/l into one or more than one fermentation vessel arranged in parallel and containing a culture with a concentration of non-flocculant yeast in the range of $10^{11}$ to $10^{12}$ cells per liter, said vessel provided with a means for stirring, and completely stirring the fermentation medium to maintain homogeneous fermentation conditions in the medium;

(b) controlling the conditions of the fermentation medium by fixing the temperature in the range of 30° to 39° C. and the pH in the range of 3.2 to 4.5;

(c) continuously removing from the fermenter a stream of wine obtained from the wort fermentation so as to keep the residence time in the fermenter fixed in the range of 4 to 9 hours; and (d) separating by means of a centrifugation separating device the stream of wine leaving the fermenter into substantially yeast-free stream and a yeast-concentrated stream, said yeast-containing stream being recirculated to the fermenter and said substantially yeast-free stream being led to subsequent processing for the recovery of the alcohol, the fermentation medium being maintained as homogeneous and constant as possible around the fermenting yeasts under all the conditions in above steps (a), (b) and (c) during the fermentation cycle.

2. A process according to claim 1, wherein the operational conditions are:

in step (a) sugar contents in the feed wort of about 130 g/l and a concentration of viable yeast cells of about $1.20 \times 10^{12}$ cells/liter;

in step (b) fermentation temperature of about 32° C. and pH of fermentation of about 4.0; and in step (c) residence time of about 6 hours.

3. A process according to claim 1 or 2, characterized in that said alcohol is ethanol.

4. A process according to claim 1 or 2, characterized in that said yeast is of the genus Saccharomyces.

5. A process according to claim 1 or 2, characterized in that the wort is fed through the top of the fermentation vessel, and the fermented wine is withdrawn from the bottom thereof.

6. A process according to claim 1 or 2, wherein the yeast-concentrated stream of step (d) is subjected to an optional treatment with an acid during a short period of time in a continuous manner to avoid the possibility of flocculation of the yeast cells, before it is recirculated into the fermenter.

7. A process according to claim 4, characterized in that the yeast is *Saccharomyces cerevisiae*.

* * * * *